(12) United States Patent
Hübner et al.

(10) Patent No.: US 7,764,374 B2
(45) Date of Patent: Jul. 27, 2010

(54) ON-CHIP SPECTROSCOPY

(75) Inventors: Jörg Hübner, Ålsgårde (DK); Anders Michael Jørgensen, Hillerød (DK); Thomas Aarøe Anhøj, Søborg (DK); Dan Anker Zauner, Copenhagen (DK)

(73) Assignee: Serstech AB, Lund (SE)

( * ) Notice: Subject to any disclaimer, the term of this patent is extended or adjusted under 35 U.S.C. 154(b) by 213 days.

(21) Appl. No.: 11/658,404

(22) PCT Filed: Jul. 14, 2005

(86) PCT No.: PCT/DK2005/000494

§ 371 (c)(1),
(2), (4) Date: Jun. 21, 2007

(87) PCT Pub. No.: WO2006/010367

PCT Pub. Date: Feb. 2, 2006

(65) Prior Publication Data

US 2008/0123095 A1    May 29, 2008

Related U.S. Application Data

(60) Provisional application No. 60/590,906, filed on Jul. 26, 2004.

(51) Int. Cl.
*G01J 3/18*  (2006.01)
*G01J 3/44*  (2006.01)
*G01N 21/65*  (2006.01)

(52) U.S. Cl. .................... 356/328; 356/301

(58) Field of Classification Search .......... 356/328
See application file for complete search history.

(56) References Cited

U.S. PATENT DOCUMENTS 6,100,541 A    8/2000   Nagle et al.
7,324,195 B2 *  1/2008   Packirisamy et al. ........ 356/328

FOREIGN PATENT DOCUMENTS

WO    WO 03/038436    5/2003

OTHER PUBLICATIONS

J. Mohr et al., "Fabrication of a Planar Grating Spectograph by Deep-etch Lithography with Synchrotron Radiation", Sensors and Actuators A, Elsevier Sequoia S.A., Lausanne, CH, vol. A27, No. 1-3, May 1, 1991, pp. 571-575.
S. Balslev et al., "Fully Integrated Optical System for Lab-On-A-Chip Applications", Micro Electro Mechanical Systems, 2004, 17$^{th}$ IEEE International Conference on (MEMS) Maastricht, Netherlands Jan. 25-29, 2004, Piscataway, NJ USA IOEEE, US Jan. 25, 2004, pp. 89-92 XP010767837.

* cited by examiner

*Primary Examiner*—F. L Evans
(74) *Attorney, Agent, or Firm*—Stephen A. Bent; Foley & Lardner LLP

(57) ABSTRACT

The present invention relates to a micro total analysis system comprising a spectroscope and a method of manufacturing such a system comprising a spectroscope in a one step process. More over the invention relates to a method of analyzing a sample in the system. The micro total analysis system comprising a spectroscope provided on a substrate and for measuring electromagnetic radiation and at least one microfluidic channel. The spectroscope comprises: a slab waveguide for guiding electromagnetic waves towards a diffraction grating dispersing the electromagnetic waves into their component wavelengths, and output means for receiving the deflected electromagnetic waves. At least a part of the microfluidic channel, the slab waveguide and the grating comprises the same main material, such as a polymer material.

33 Claims, 10 Drawing Sheets

ON-CHIP SPECTROSCOPY

FIELD OF INVENTION

The present invention relates to a micro total analysis system comprising a spectroscope and a method of manufacturing such a system comprising a spectroscope in a one step process.

BACKGROUND OF THE INVENTION

Micro total analysis systems (µTAS) are becoming more widely used, and further still more features are built into such systems. The systems may be used for fast analysis of small volumes of fluids. The micro systems comprise microfluidic channels and reaction chambers and also functional elements such as mixers, pumps and separation may be integrated on the chip. The detection of properties of fluids or fluid components is dominated by optical methods, such as fluorescence detection or absorption spectroscopy.

Typically, the optical systems are provided at a separate device or only partly integrated with the fluid handling system. There has been a strong effort to integrate parts of the optical system, such as waveguides with the fluid handling system, so that light may be provided to the sample to be analyzed and the resulting light, the sample light, resulting from the interaction between the incident light and the sample may be re-collected via integrated waveguides.

However, connection to external or off-chip active optical elements, such as light sources, detectors, spectroscopes, etc. is usually a demanding task, requiring precise alignment between the fluid handling chips and e.g. optical fibers connecting chip with the off-chip optical elements. The lack of precise alignment may result in loss of too much signal light to be able to practically detect the often weak optical responses from the sample.

Sample detection can be done using a wide variety of detection methods, and often a spectroscopic method is used. The spectroscopic methods may include simple fluorescence measurements, conventional absorption spectroscopy and advanced laser spectroscopy methods.

SUMMARY OF THE INVENTION

It is an object of the present invention to provide for a system combining a fluid handling system with an optical spectroscope for analyzing a sample in a fluid channel.

According to a first object of the present invention, a micro total analysis system is provided, wherein the system comprises a spectroscope provided on a substrate and for measuring electromagnetic radiation, the spectroscope comprises:
  a slab waveguide for guiding electromagnetic waves towards a diffraction grating dispersing the electromagnetic waves into their component wavelengths, and
  output means for receiving the deflected electromagnetic waves, at least one microfluidic channel and wherein at least a part of the microfluidic channel, the slab waveguide and the grating comprises a main material.

Typically, the output means outputs the waves from the spectroscope to one or more receiving means.

The at least a part of the microfluidic channel, the slab waveguide and the grating may be one monolithic element and thus be fabricated using a simple manufacturing process, not requiring each part of the system to be manufactured in more or less separate process steps on the same substrate.

The spectroscope and the at least one microfluidic channel may be interconnected by an interconnecting waveguide guiding electromagnetic waves from the at least one microfluidic channel to the slab waveguide, i.e. to the spectroscope for detection of light emitted from the at least one microfluidic channel. The interconnecting waveguide may form part of the monolithic element.

In an embodiment of the invention, the at least part of the microfluidic channel, the slab waveguide and the grating, and preferably also the interconnecting waveguide, comprise a main material being glass or polymer and preferred are the elements manufactured in glass or in a polymer, such as PMMA, such as a radiation definable polymer, such as SU-8, or an SU-8 based polymer. The use of a radiation definable polymer provides a number of advantages during processing of the system and definition of the structure. In another embodiments may at least part of the microfluidic channel, the slab waveguide and the grating, and preferably also the interconnecting waveguide, comprise a main material being suitable for moulding, such as injection moulding or embossing moulding, such materials may be polycarbonate, PC, or cyclo-olefin-copolymer, COC, or a material based on these materials.

In the micro total analysis system, the microfluidic channel may comprise an analysation channel part, and electromagnetic radiation may be emitted from or transmitted through the analysation part of the channel. Typically, the emission of the electromagnetic wave is due to an interaction between an incoming electromagnetic wave and a fluid, such as a gas or a liquid, or fluid components, such as bacteria, etc., present in the fluid channel and the electromagnetic wave is thus emitted from the analysation part of the channel in response to an incoming electromagnetic wave. Furthermore, the transmitted electromagnetic waves may be at least partly absorbed by the fluid or by fluid components, so as to provide an absorption spectrum of the fluid and/or its components. The emitted electromagnetic wave may be emitted from the fluid by fluorescence, by elastic or inelastic (Raman) scattering, or in any other way be a modified version of the incoming wave.

The interconnecting waveguide is adapted to receive the electromagnetic radiation emitted from or transmitted through the microfluidic channel and is thus positioned in electromagnetic communication with the analysation part of the channel, to thereby allow for coupling of electromagnetic waves from the analysation part of the channel to the interconnecting waveguide.

The electromagnetic waves in the system do preferably propagate within the main material due to a higher index of refraction of the main material in relation to the surrounding material. In a preferred embodiment the surrounding material is air, but it is envisaged that any cladding allowing for confinement of the electromagnetic waves in the interconnecting waveguide, the slab waveguide, and possible also in any integrated output means, may be used.

The electromagnetic waves are coupled from the interconnecting waveguide into the slab waveguide at the slab waveguide end of the interconnecting waveguide. To form an entrance slit, a tapered section of the interconnecting waveguide may be positioned adjacent to the slab waveguide. The structure may be optimized so that the electromagnetic waves are coupled into the slab waveguide without significant losses upon coupling between the waveguides.

It is preferred that there is a light frequency dependent element between the microfluidic channel and the grating, and even more preferred is the light frequency dependent element positioned in the interconnecting waveguide. The light frequency dependent element may comprise, or be, a filter. This element may ensure that backscattered light or backscattered electromagnetic waves from any external sources or any backscattered electromagnetic waves from any sources providing incident electromagnetic waves to the micro fluidic channel, and especially to the analysation part of the channel are filtered off in the interconnecting waveguide so that no unwanted scattered signal disturbs the spectroscopic determination. Thus, the light frequency dependent element may be designed so as to reduce the optical power at the light frequency emitted by any external or internal light sources used to excite a fluorescence or Raman signal.

The light frequency dependent element may be inserted in a groove crossing the interconnecting waveguide.

The grating may be positioned in relation to the interconnecting waveguide so that the electromagnetic waves scattered from the interconnecting waveguide is incident at the grating. They may be directly incident on the grating or indirectly incident e.g. via multiple reflections in the slab waveguide. In a preferred embodiment, the grating is positioned in the slab waveguide opposite the entrance slit of the interconnecting waveguide.

The grating is formed of grooves in the slab waveguide preferably utilizing total internal reflection at the boundary formed between the slab waveguide and the surrounding cladding. The grating may be reflective or transmissive, however, when miniaturizing the system, it is often preferred to use a reflection grating to reflect incoming waves back into the slab waveguide. In other embodiments, a transmissive grating may be advantageous, e.g. depending on external receiving means.

The resolution of a spectroscope as provided by the grating in the slab waveguide is an important parameter, and the resolution is defined by a combination of entrance slit width, number of illuminated grating grooves, grating period and grating order. These parameters may not necessarily be independent of each other, so that the adaptation of the resolution to a desired application is a complex procedure. It is not straight forward to miniaturize a spectroscope, since the resolution of the spectroscope is proportional to the number of illuminated grating grooves so high resolution may require a certain grating size, and furthermore, are the output means and/or receiving means in an integrated device preferably performed without moving devices, such as moving mirrors, and instead the receiving means comprises a diode array e.g. in an optical multi channel acquisition (OMA) configuration. The size of the diode array and thus the number of channels is limited due to the size restrictions of the integrated device, and thus a trade-off between resolution and spectral bandwidth may be required to obtain a certain size.

However, for a spectroscope integrated with a micro total analysis system or adapted to be used with a so-called lab-on-a-chip system, the typically applications for the spectroscope comprises absorption and fluorescence spectroscopy, surface enhanced Raman (SER) spectroscopy among others and typically, the specific lab-on-a-chip is designed to be used with a limited range of applications. The spectroscope may thus be optimized to these applications, so that e.g. a higher resolution may be obtained if a shorter free spectral range is acceptable or vice versa. It is an advantage of using SER spectroscopy on a lab-on-a-chip system or in a micro total analysis system that the wavelength of the Stokes lines of a Raman spectrum typically are spectrally in rather close vicinity from the excitation laser line. The distance of the Stokes or Raman lines from the excitation light is generally known and the spectroscope may thus be designed to operate in a window of limited bandwidth and high resolution.

The close vicinity of the Stokes line to the laser excitation light makes the use of a filter between the microfluidic channel and the grating, e.g. in the interconnecting waveguide, even more preferred in order to separate the weaker Raman scattered light from the strong Rayleigh scattered laser light of the incident light beam.

Another important parameter for the grating is the linear dispersion, which provides a measure of the spatial separation of the spectral components and is expressed in $\mu m/nm$. A linear dispersion of 10 $\mu m/nm$ means that components of the input waves that are spectrally 1 nm apart will be separated by 10 $\mu m$ at the spectroscope output, i.e. at the output means.

The grating design is thus very important to provide an integrated spectroscope that will provide a sufficient resolution for the specific application. It is presently preferred that the grating is concave so that electromagnetic waves diffracted and deflected from the grating are focused towards the output means, and furthermore, that the grating is an echelle grating in the Littrov configuration, see e.g. K. A. McGreer, IEEE Phot. Techn, Lett. Vol. 7, No. 3, 1995. Using this configuration, the output means in the form of waveguides are preferably arranged on the Rowland circle of the grating ensuring that the dispersed electromagnetic waves are focused on the output means. In another embodiment, the grating is modified so that the dispersed electromagnetic waves are focused on a straight line so that the output means may be positioned on a straight line, instead of on the Rowland circle. However, providing the output means in the same main material as the slab waveguide does provide for an increased freedom in positioning of the output means, which then also provides for an increased freedom in designing the grating.

To keep the transmission losses at a minimum and improve the grating efficiency, the effect of total internal reflection may be used. The grooves of the grating may be formed so that the angle of incident waves is below the maximum angle for total internal reflection. Thus, the total internal reflection may be maximized by adjusting the shape and angle of the grating grooves or the periodic grating elements of the grating. Among other methods, this maybe obtained by allowing the waves to be reflected more than once at each groove. To further improve the efficiency of the grating, and thus of the spectroscope, the backside of the grating may be metallized.

The grating is preferably provided in the slab waveguide simultaneous with the manufacturing of the slab waveguide and the grooves defining the grating may be from 1-50 $\mu m$, such as from 10-50 $\mu m$, such as 10 $\mu m$, such as 30 $\mu m$, such as 40 $\mu m$, deep, transverse to a surface of the slab waveguide. The echelle grating provides a grating wherein the grooves in the plane of the spectroscope may be from around 1 $\mu m$ to 20 $\mu m$ depending on the order the spectroscope is to be working in and the required resolution and linear dispersion.

The output means may be positioned anywhere on the Rowland circle, however, in preferred embodiments they are positioned substantially opposite to (i.e. about 180° to) or substantially rectangular (i.e. about 90°) to the grating, thus being 85-95-°, such as 90°, or 175 to 185°, such as 180° to the grating. Alternatively, may the output means be positioned at an angle in the interval between 0 to 20° to the grating. It may be an advantage to position the output means at a low angle to the grating since a compact device may be provided.

The output means may comprise waveguides or an array of waveguides and may represent waveguides of an optical multichannel acquisition array. The output means may also have a tapered section so to form an output slit of the spectrometer.

The output means may connect to one or more receiving means, such as light sensitive semiconductor devices, such as photodiodes, such as array of photodiodes, such as a CCD, such as backside contacted photodiodes, etc.

The substrate may be a glass substrate, a polymer substrate, or preferably a semiconductor substrate, such as a GaAs substrate or a silicon substrate.

The output means and/or the receiving means, such as the one or more light sensitive semiconductor devices may be formed integrated with the semiconductor substrate.

Especially, when using a silicon substrate, the light sensitive devices may be easily integrated with the substrate and the µTAS.

The interconnecting waveguide may be a multimode waveguide, thus the height of the waveguide may be selected so that multiple modes may be confined in the waveguide. It is an advantage of the system that the interconnecting waveguide may be selected to have the same height as the depth of the at least one microfluidic channel. Hereby may the microfluidic waveguide and the interconnecting waveguide be formed in one step without the need for additional steps reducing the height of the interconnecting waveguide. Furthermore, to obtain a reliable response from the analysation part of the microfluidic channel, it is preferred that the emission signal is collected from the entire depth of the microfluidic channel. The height of the interconnecting waveguide is selected between 1 µm and 50 µm, such as between 10 µm and 40 µm, such as between 20 µm and 30 µm. The interconnecting waveguide may have a rectangular cross section with a side length of at least 2 µm, such as at least 10 µm, such as at least 25 µm, such as 30 µm, such as at least 40 µm, such as 40 µm, such as at least 50 µm.

Preferably, the height of the waveguide is selected to correspond to the depth of the microfluidic channel. The depth of the microfluidic channel is selected according to the specific application(s) for which the system is designed. When the system is e.g. used to scan fluids comprising bacteria, the dimensions of the microfluidic channel should thus preferably not be less than 10 µm×10 µm to ensure a non-interrupted flow in the channel. Convenient for most practical purposes would be a cross section of 40 µm×40 µm. Often the channel is selected to be quadratic, however also other forms of the channel may be used, such as rectangular channels having e.g. side lengths of 10 µm×40 µm, 40 µm×60 µm, etc. Typically, a side length being at least 10 µm, such as at least 40 µm, such as at least 60 µm, such as at least 100 µm may be used.

The incident electromagnetic waves are preferably directed towards the analysation part of the channel may be an external waveguide or it may be an electromagnetic source integrated with the system or provided on the same substrate.

The typical applications for the spectroscope comprise absorption and fluorescence spectroscopy, surface enhanced Raman spectroscopy among others. For example a fluid or fluid components present in the microfluidic channel may absorb at least a part of the incoming electromagnetic radiation, so that the electromagnetic radiation emitted from the microfluidic channel represents an absorption signal representing the fluid and/or its fluid components. Another example is the fluorescence measurements, wherein a fluid or fluid components present in the microfluidic channel emit a fluorescent signal in response to the incoming electromagnetic wave so that the electromagnetic radiation emitted from the microfluidic channel provide a fluorescence signal representing the fluid and/or its fluid components.

In a specific embodiment, the signal may be a Raman signal representing the fluid and/or its fluid components, and it may further be a surface enhanced Raman signal.

The Raman spectrum is formed by the inelastic scattering of photons (e.g. of an incoming electromagnetic wave) with vibrational energy levels of a molecule. The scattered light may be regarded as being modulated by the molecule vibrations, resulting in several side bands in the frequency space, where the distances between the excitation light and side bands correspond to vibrational frequencies of the molecule vibrations. The vibrational states are very specific to the molecule so that the Raman spectra of a molecule is often referred to as a finger print of the molecule. However, Raman cross-sections are inherently weak and an amplification of the effect may be necessary. Such an amplification of the effect has been seen by bringing the molecule under investigation in close vicinity to metal nanoparticles whereby the Raman signal may be significantly enhanced. The method is called Surface Enhanced Raman Spectroscopy, SERS, and is usually carried out on a nanostructured substrate or in a solution containing colloid silver (or gold) nanoparticles.

The SERS method may be used with a large range of applications, including clinical and biological applications, such as forensic clinical and biological applications, genomics applications, for DNA hybridization, analysis and monitoring of waste water, body fluids, etc.

In the present invention, it is preferred to provide at least one area of the microfluidic channel, in the analysation part, with a nanostructured surface. The nanostructured surface is preferably metallized with Ag, Au, Cu, etc., or any other metal capable of inducing SERS and/or any combination of such materials.

The SERS active surface, i.e. the nanostructured surface, may be provided in a variety of ways. It may be a metal island film, a metal coated nanosphere structure, a metal coated random nanostructure, a metal nanoparticle embedded polymer coating, wherein metal nanoparticles are provided in a polymer layer, a nanostructure induced by E-beam lithography or any other surface capable of enhancing the Raman signals.

The nanostructured surface provides for an amplification of the Raman signal so that a surface enhanced Raman signal is provided.

The incident electromagnetic waves are preferably directed towards the nanostructured surface(s) of the analysation part of the channel.

The light scattered from the nanostructured surface may be collected from the nanostructured surface and guided through the interconnecting waveguide to the spectroscope. Similarly may any other signals emitted from the microfluidic channel, by transmission/absorption, fluorescence, or any other means be collected and guided through the interconnecting waveguide to the spectroscope.

The interconnecting waveguide may preferably be positioned in electromagnetic communication with the analysation part, so that e.g. the interconnecting waveguide abuts the analysation part of the microfluidic channel.

In a preferred embodiment the height of the interconnecting waveguide and the depth of the microfluidic channel are substantially the same so that the interconnecting waveguide abuts the microfluidic channel in the entire height of the channel.

To obtain an efficient collection of electromagnetic radiation from the channel to the waveguide, it is preferred that the numerical aperture of the interconnecting waveguide is high. Preferably, the numerical aperture of the interconnecting waveguide is selected so as to maximize electromagnetic radiation coupled from the microfluidic channel to the interconnecting waveguide.

The microfluidic channel may form part of a larger micro analysis system comprising one or more analysation parts and a number of microfluidic channels, mixers, pumps, separation channels, etc. and the fluid may be flowing in the microfluidic channel during analysis, or the fluid may be held in the microfluidic channel during analysis. Alternatively, the microfluidic channel may be used as a cuvette. Hereby, no other pumps, mixers, etc. may be necessary in order to perform the analysis.

The micro total analysis system may be a multiple use system or it may be a single-use system.

The spectroscope may further be used as a demultiplexer. It is an advantage of using the spectroscope as a demultiplexer for example when a fluid and/or its fluid components are analyzed using multiple fluorescent markers. Using the spectroscope as a demultiplexer then provides for a separation of the different fluorescence wavelengths at the spectroscope and thus for a separate output of the different wavelengths at the output means.

According to another aspect of the present invention, a method of analyzing a sample in a micro total analysis system is provided, the method comprises the steps of emitting incident electromagnetic waves to a sample in an analysation part of a microfluidic channel, collecting the response electromagnetic waves emitted from the sample in response to the incident electromagnetic waves by an interconnecting waveguide, guiding the response electromagnetic waves through the interconnecting waveguide to a slab waveguide, guiding the response electromagnetic waves through the slab waveguide for dispersion at a grating, receiving the dispersed electromagnetic waves at output means for outputting the dispersed electromagnetic waves.

According to a further aspect of the present invention, a process for manufacturing a micro total analysis system is provided, the process comprises the steps of providing a layer of a main material on a substrate,
masking the main material to indicate a pattern,
defining the pattern by way of etching or developing to form a slab waveguide, a grating formed in the slab waveguide, and at least one microfluidic channel, and
providing a lid to at least the microfluidic channel.

The main material may be glass, such as borosilicate glass or a polymer, and in a preferred embodiment, it is a radiation definable polymer, such as a photodefinable polymer. A radiation definable polymer is a polymer which in the unexposed state is sensitive to radiation so that the radiation definable polymer may be defined, that is in a specific form or shape, by irradiating parts of the polymer while leaving other parts unexposed. During exposure or by further processing, such as by heating or baking, either the exposed or the unexposed parts (positive or negative process) become crosslinked whereafter the crosslinked polymer is no longer radiation definable and thus no longer radiation sensitive.

When the main material is a photosensitive polymer, the process becomes a simple process not necessarily involving any etching steps. Thus, according to an embodiment of the second aspect, a process for manufacturing a micro total analysis system is provided, wherein the process comprises the steps of providing a layer of a radiation definable polymer on a substrate,
patterning the radiation definable polymer through exposing,
developing the patterned radiation definable polymer to form a slab waveguide, a grating formed in the slab waveguide, at least one microfluidic channel, and optionally
providing a lid to at least the microfluidic channel.

An intermediate layer may be provided between the layer of the main material and the substrate before the main material is provided on the substrate, the intermediate layer being a layer with a refractive index less than the refractive index of the main material so as to ensure that light is, at least substantially, confined within the main material.

In the same process, an electromagnetic waveguide interconnecting the slab waveguide and the microfluidic channel may be provided. The interconnecting waveguide may thus be manufactured in the same main material as the slab waveguide, the grating formed in the slab waveguide, and the at least one microfluidic channel.

Furthermore, another waveguide may be fabricated in the same process, this waveguide being adapted to guide incident electromagnetic waves to the microfluidic channel, preferably to an analysation part of the microfluidic channel.

The substrate may be any substrate capable of supporting the layer of the main material. The substrate may be glass, polymer, ceramic, plastic, preferably a semiconductor, such as GaAs, GaInAsP, preferably such as silicon.

The radiation definable polymer may be definable by photo lithography, e-beam lithography, X-ray lithography, ion-beam lithography, near UV-lithography, or hot embossing or nano-imprinting lithographies. Preferably, the radiation definable polymer is definable by photo-lithography so that standard optical lithography using I-line lithography (i.e. an exposing light beam at a wavelength of about 370 nm) may be used, thus enabling integration with further elements on a chip system.

The polymer is preferably a solid polymer. The radiation definable polymer may be a negative tone resist, such as SU-8, whereby the unexposed part of the polymer is removed during development of the structure. However, it may also be a positive tone resist.

To obtain a structure being chemically stable, an epoxy based radiation definable polymer, may be used. During exposure, and typically also a post exposure bake step, the epoxy based polymer is cross-linked and very strong bonds are formed in the epoxy based polymer making the structure suitable for fabrication of many kinds of structures.

It is preferred that the radiation definable polymer is photodefinable, preferably by an electromagnetic source having a wavelength at 248 nm, (excimer) a wavelength above 248 nm, such as above 250 nm, such as above 280 nm, such as above 300 nm, such as above 320 nm, such as above 350 nm, preferably about 370 nm, used in I-line lithography.

It is an advantage of being able to use standard photolithography that the integration with any other devices on a chip is much less complicated when standard manufacturing methods may be used. It reduces the complexity of the fabrication process and thus further reduces the cost of the final sample. And since the costs of e.g. single use samples need to be reduced in order to allow for widespread use of such single use devices, reduction of the manufacturing costs are an essential need for the continued growth of the market for such devices.

The layer of the main material may have a thickness of at least 10 µm, such as at least 25 µm, such as 30 µm, such as at least 40 µm, such as 40 µm, such as at least 50 µm.

The process may further comprise the step of providing a cladding around the micro total analysis system, and the cladding does preferably have a refractive index being less than the refractive index of the radiation definable polymer. It is preferred to provide a cladding in a non-stress inducing way so that the stress applied to the structure by the cladding is minimized.

Furthermore, the process may include the fabrication of output means. The output means may comprise waveguides, such as an array of waveguides. In a preferred embodiment, the output means waveguides are also manufactured in the main material so that the output means may be fabricated simultaneous with the fabrication of the slab waveguide, grating, any interconnecting waveguide(s) and the at least one microfluidic channel.

The system may also be provided with a lid, such as a glass lid. The lid may be bonded to the system, to the waveguides and any cladding material, so as to form a substantially closed microfluidic channel.

The lid may comprise a substrate of e.g. glass, and any intermediate material providing a top cladding for the waveguide. Using e.g. a glass lid on a polymer micro total analysis system, it is preferred to coat the glass substrate with a polymer layer, such as PMMA, so that this polymer may be bonded to the main material, i.e. the polymer, and form a top cladding.

The microfluidic channel may further comprise a channel inlet for introducing a fluid into said microfluidic channel, and in some embodiments also a channel outlet may be provided.

In a further aspect of the invention is provided a process for manufacturing the micro total analysis system by means of a moulding technique. In the process the main material is provided into a mould so that at least part of the microfluidic channel, the slab waveguide and the grating are formed in one piece. The moulding technique may be an injection moulding technique or an embossing moulding technique. The moulding may be a sequential moulding process. A sacrificial layer, or anti-sticktion layer may be provided to the mould so as to facilitate release of the moulded system.

The main material may be injected into the mould at high pressure, and possible at elevated temperature. The mould may be fabricated in Silicon, in a metal or in any other suitable material.

The invention is described by the description of a micro total analysis system, a method of analyzing a sample in such a system and a process for manufacturing such a system, and it is envisaged, that features described in relation to one aspect only, may also be applied to other aspects of the invention as herein described.

BRIEF DESCRIPTION OF THE DRAWINGS

Embodiments of the invention will be described, by way of example only, with reference to the drawings, in which.

DESCRIPTION OF EMBODIMENTS

Figure 1:
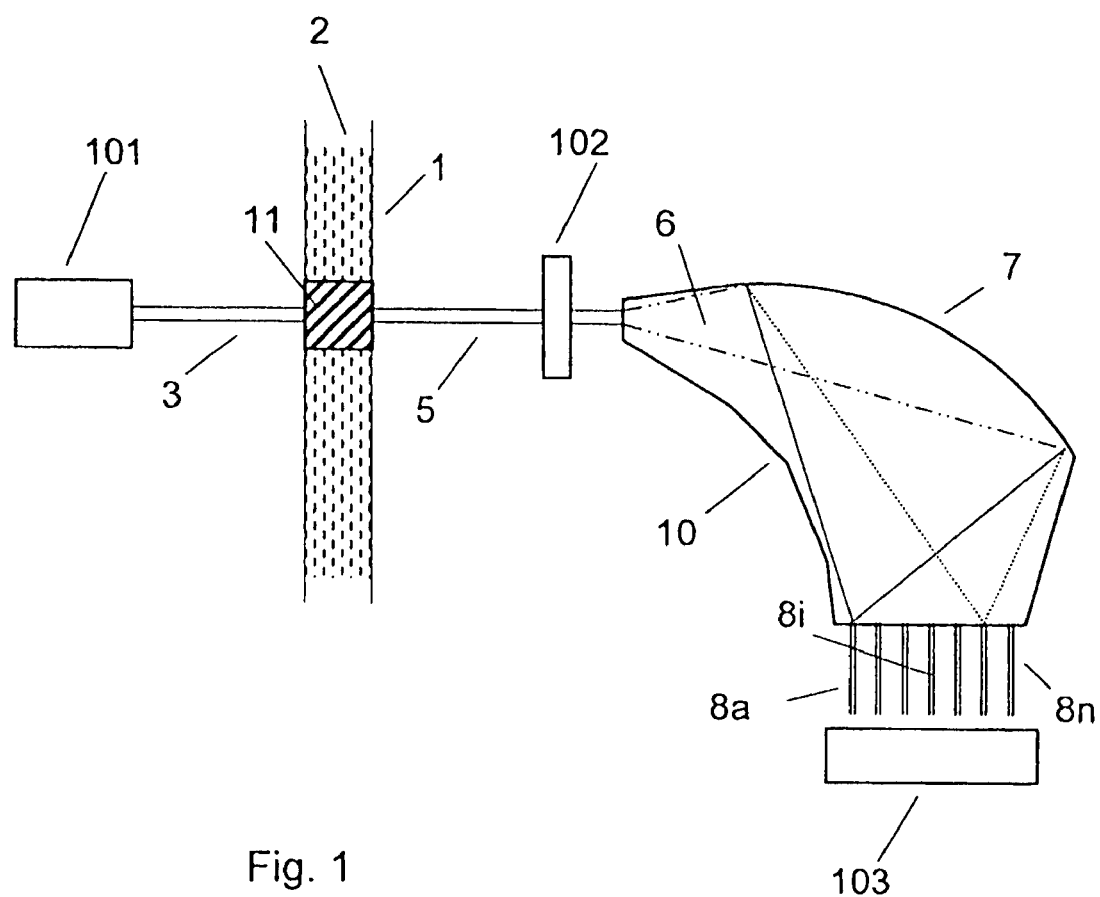
FIG. 1 shows a schematic view of a micro total analysis system configured for absorption spectroscopy.

In FIG. 1, a micro total analysis system or at least a part of such a system is shown. The microfluidic channel 1 may comprise a fluid 2, being a gas or a liquid, to be analyzed.

The system in FIG. 1 is configured for absorption spectroscopy and a first optical waveguide 3 provides an incident electromagnetic wave to the fluid 2 in the analysation part 4, being substantially the exposed area of the channel. The incident electromagnetically wave is typically monochromatic light, such as a laser light. The electromagnetically wave may in a given embodiment be emitted from an external light source 101 or from a integrated light source 101. In a situation of fluorescence and Raman measurements may the electromagnetic wave also be launched through a transparent substrate or lid perpendicular to the channel 1. Typically, a part of the incident light will interact with the fluid and/or fluid components and be at least partly absorbed by the fluid or the fluid components. The resulting light transmitted through the channel is then collected by the interconnecting waveguide 5. The waveguide 5 is typically a waveguide supporting multiple modes, and guides the light transmitted through the channel to the spectroscope 10, the spectroscope comprising the grating 7 and the slab waveguide 6 guiding the light beam towards the grating 7. In this embodiment the grating is a concave echelle grating in the Littrov configuration, and the light beam incident on the grating is dispersed and focused on the output facet of the spectroscope and output means 8a, . . . 8i, . . . 8n are provided to collect the output beams. The waveguide 5 may include a light frequency dependent element, e.g. a filter 102, such a filter may be completely integrated or provided as an external element, possible for inserting in a groove crossing the waveguide. The light frequency element may e.g. also be placed at the output means. A filter may be provided to further reduce backscattered incident light that is scattered back into the detector/spectroscope. As is seen from the figure, the output means are arranged on a straight line and the component elements of the deflected light beam are each focused on a specific output means. The output means 8 are here selected to be waveguides guiding the output to output means, such as photodetectors 103 for detection of the signal. The output means may be, or be connected to, light sensitive semiconductor devices, such as photodiodes, arrays of photodiodes, CCDs etc. In a situation where the substrates is a silicon substrate, such devices may be formed integrated with the substrate. The output means may also be positioned on the Rowland circle.

The analysation part is the area of the microfluidic channel wherefrom the transmitted, emitted or re-emitted electromagnetic waves are collected by the interconnecting waveguide. Thus, the analysation part is dependent on both the numerical aperture and the dimensions of the interconnecting waveguide, the area exposed by the incident light beam, etc. Typically, when a SERS analysis is to be carried out, the area of the microfluidic channel provided with nanostructured wall(s) is larger than the area from where the resultant Raman signals are collected by the interconnecting waveguide. This ensures a uniform radiation signal and does also ensure a maximum signal output. The waveguides 3 and 5 need not be straight lines.

Figure 2:
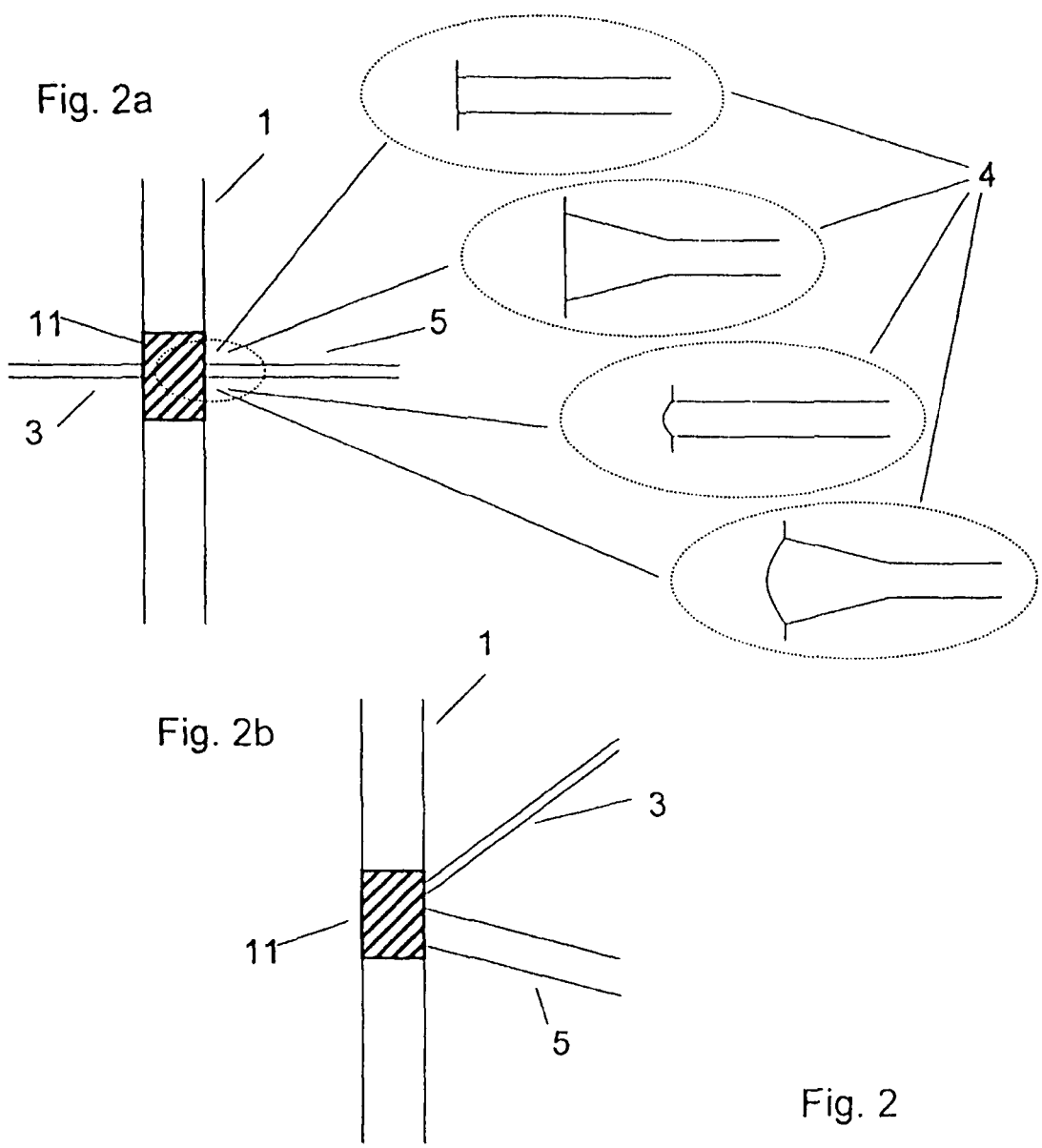
FIGS. 2a and 2b shows schematically possible configurations for absorption measurements and for SERS or fluorescence measurements, respectively.

FIG. 2a shows the configuration of waveguides and channel in more detail, and it is seen that the interconnecting waveguide 5 is positioned substantially across the microfluidic channel from the first waveguide 3 providing the incident light beam. In this way, when the interconnecting waveguide collects the light beam transmitted through the channel and when the incident light beam is known, may an absorption spectrum be determined at the spectroscope. The analysation part 11, or interaction region/detection area, is thus primarily the area between the two waveguides 3, 5. However, due to scattering of the light and depending of the numerical aperture of both the first waveguide 3 and the interconnecting waveguide 5, the part of the fluid actually being analyzed may be longer than the width of the two waveguides. The two waveguides may have the same dimensions, but may also be of different dimensions. The interconnecting wave guide may be adapted to receive electronic radiation, e.g. by adapting the geometry of the wave guide 4 at the interface to the fluidic channel. In the figure is four different layouts illustrated. These layouts are examples and the invention is not limited to these layouts.

FIG. 2b shows another configuration of the waveguides and channels, particularly well suited for fluorescence and SER spectroscopy.

The first optical waveguide 3 provides the light to the analysation part of the microfluidic channel at an angle to the interconnecting waveguide. When analyzing the fluid with fluorescence or SERS, it is preferred to avoid or at least to minimize the amount of incident light coupled into the interconnecting waveguide. Any incident light coupled through the interconnecting waveguide to the detection means, i.e. the spectroscope, provides a false signal to the output means and since the incident light is often much stronger than the surface enhanced Raman signals or fluorescent signals, the real signals may not be recognizable due to the noise from the incident light guided all through the system. It is therefore preferred to couple the incident light into the microfluidic channel so that as small an amount as possible is collected by or coupled into the interconnecting waveguide 5. It is however envisaged that the incident light may be coupled into the channel from any source and from any angle. Thus, the incident light may be guided in or on the substrate from any external or on-chip light source. Alternatively, may the incident light be coupled in to the channel via a lid transparent to the incident light, such as via a glass lid. The waveguides 3, 5 may or may not have the same width.

Figure 3:
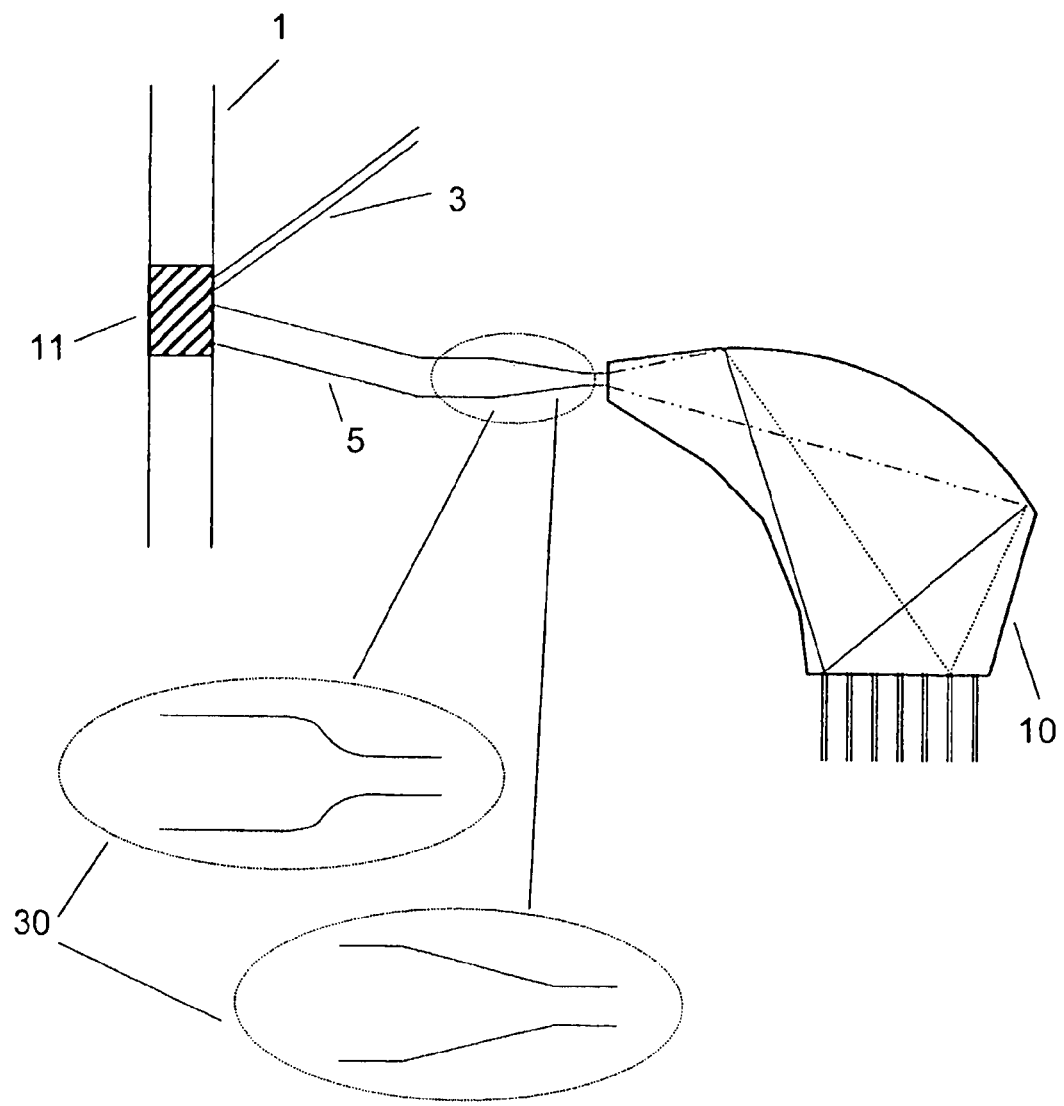
FIG. 3 shows a configuration for SERS or fluorescence measurement, wherein further a spectroscope entrance slit is seen.

FIG. 3 shows a micro total analysis system configured for fluorescence or SER spectroscopy and same referral numbers as used above are used for the same elements. It is seen that there is a slit entrance 30 from the interconnecting waveguide into the slab waveguide. Two embodiments of suitable slit entrances are illustrated. The slit entrance is provided as a tapering of the waveguide to provide for a proper injection of the light into the slab waveguide. Also other means of providing an entrance slit may be envisioned, alternatively, a tapering may not be provided.

Even though the microfluidic channel in the drawings are shown as straight channels, it is envisaged that other forms of the channel may be equally used. For example, a U-formed channel may be provided and e.g. an absorption measurement may be performed by providing incident light to one end of a leg of the U-form, transmitting/absorbing a part of the light beam during light beam traversing of this channel leg and measuring the transmitted light at the other end of the said channel leg.

Figure 4:
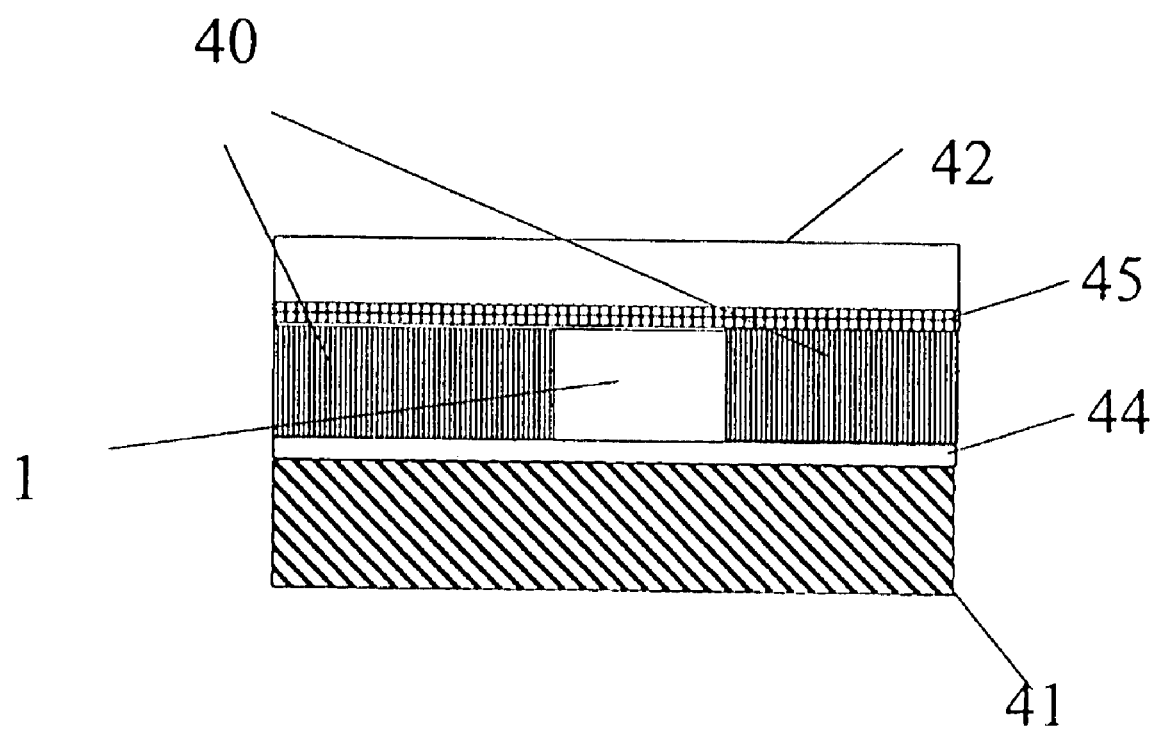
FIG. 4 shows a cross sectional view of a microfluidic channel of the μTAS system.
Figure 5:
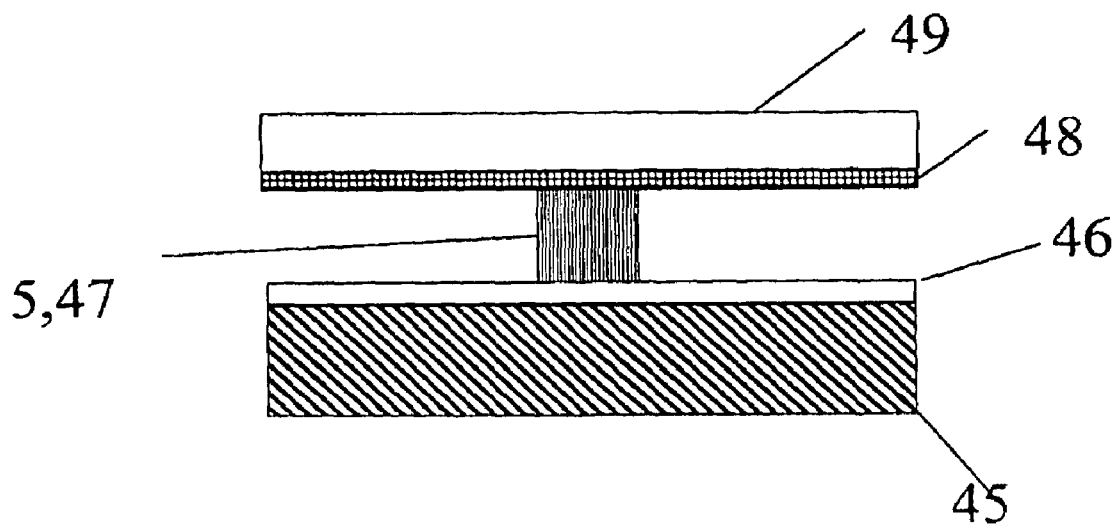
FIG. 5 shows a cross sectional view of the interconnecting waveguide of the μTAS system.

FIG. 4 shows a cross section of the microfluidic channel in a preferred embodiment. The microfluidic channel 1, and the surrounding material 40 is shown. The surrounding material is provided on a substrate 41 and a lid 42 closes the channel. An intermediate layer 44 may be provided between the substrate 41 and the surrounding material. In FIG. 5, a cross section of the interconnecting waveguide 5 is shown. It is seen that the waveguide is provided on a substrate 41 and the material 40 surrounding the microfluidic channel is also used for the interconnecting waveguide 5.

The intermediate layer, as illustrated in FIGS. 4 and 5, may be a $SiO_2$ layer, e.g. If the substrate is a silicon substrate, or the intermediate layer may be a PMMA layer, e.g. if the substrate is a glass substrate. If the substrate is a silicon substrate, the intermediate layer may be provided in order to ensure the light propagates within the waveguide, since the refractive index of silicon being 3.6 is higher than the refractive index of SU-8 being 1.6. The refractive index of $SiO_2$ being 1.46. If the substrate is a glass substrate, the intermediate layer may be provided in order to ensure adherence of the SU-8 on the substrate.

An intermediate layer 45 may also be provided between the surrounding material and the lid. This layer may be provided in order to ensure adherence of the lid.

The spectrometer may be easily integrated with the interconnecting waveguide, microfluidic channels, etc. without additional process steps because the microfluidic system are based on the same material platform. The process of manufacturing the micro total analysis has been performed as described in the following:

The substrate 45 is chosen to be silicon. It provides many advantages in using a standard silicon wafer as basis substrate since many of the well developed Si-processes may then be used for processing of both the micro total analysis system and any further detectors, light sources, etc.

The Si wafer 45 is oxidized at high temperature until the oxide layer 46 has grown to a thickness of 3 micrometer. Upon this oxidation is the wafer subjected to a dehydration bake for several hours at temperatures exceeding 200 deg. C. The wafer is cooled down and an epoxy based photoresist 47 is spun onto the oxidation layer. The spin speed determines the layer thickness and depending on the viscosity of the resist the spin speed is about 2000-3000 rpm. The oxide layer has a refractive index of about 1.46 (at 633 nm) which makes is suitable as a lower cladding for the waveguides.

After spin-on of the photoresist, the wafer is soft baked on a hotplate at 65 deg. C. for 2 minutes and then at 95 deg. C. for another 6 minutes. The photo-resist is then exposed through a suitable mask. The exposure wavelength range is selected to be the so-called I-line (350 nm-400 nm) and the exposure dose is about 250 $mJ/cm^2$.

Upon exposure, the wafer is subjected to a two step post exposure bake, the first step being about 1 minute at 65 deg. C. and the second step being another 5 minutes at 95 deg. C. After exposure and post exposure bake, the wafer is developed in a suitable developer (preferably, the developer product recommended by the photoresist manufacturer). The development time is about 6 minutes and is followed by a rinse in isopropanol and a drying of the surface using a nitrogen stream.

To prepare the lid, a boro silicate glass wafer 49 is cleaned and a thin layer of about 5-7 μm of PMMA 48 is spun on. The glass wafer is then with the PMMA layer facing down is then brought into contact with the polymer layer of the silicon wafer. This wafer stack is placed in a bonding machine where glass lid and silicon wafer are pressed together at a temperature of 100 deg. C., thus using thermal bonding. This thin PMMA layer having a refractive index of about 1.46 serves as the top cladding for the waveguide. After cooling down, the components are diced out using a standard semiconductor grade dicing saw.

In a preferred embodiment, the photoresist is a negative epoxy based photoresist, such as SU-8. SU-8 is a material having a high aspect ratio imaging, and having a good chemically and thermally resistance. The refractive index of SU-8 is about 1.6. Thus, SU-8 provides a good beam confinement when surrounded by air. However, it is envisaged that also a cladding material having a refractive index being lower than the refractive index of SU-8, such as e.g. glass may be used, such as for example a glass having a refractive index of 1.45. In one embodiment, the excitation laser light is a GaAs/GaAlAs laser diode providing a laser beam of 785 nm. It is an advantage of using such a near infrared laser light that no fluorescence is induced during analysation using Raman scattering, so that the Raman spectrum is not influenced by fluorescence noise.

Figure 6:
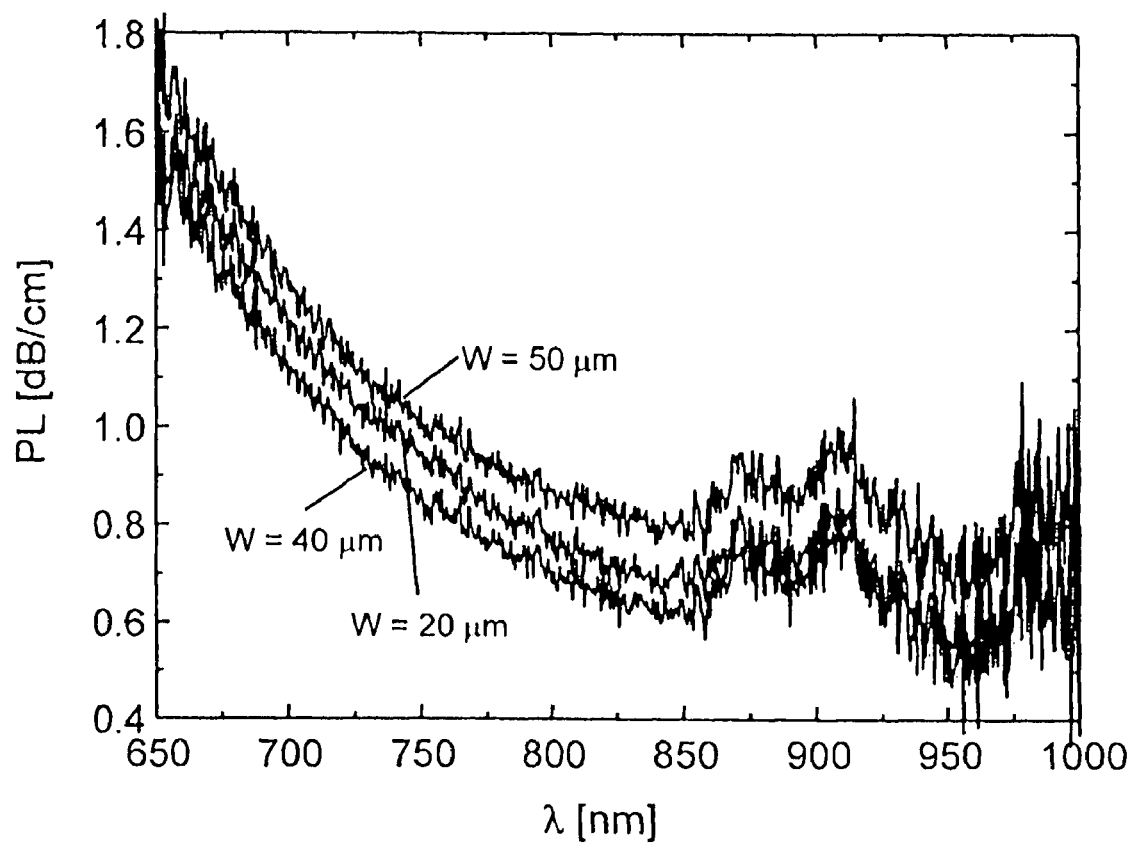
FIG. 6 shows the propagation loss of a polymer waveguide.

The structures fabricated using the above process have been characterized and also the propagation loss of SU-8 waveguides have been evaluated. In FIG. 6, measured propagation loss, PL, of SU-8 waveguides of various horizontal dimensions, w, are shown. The horizontal dimensions of the measured waveguides are 20 μm, 40 μm and 60 μm, respectively and it is seen that the measured propagation loss is about 0.8 dB/cm around 800 nm. It is seen that the propagation loss varies from about 1.7 dB/cm around 500 nm to about 0.5 dB/cm around 1100 nm. It is further seen that the propagation loss is substantially constant from about 800 nm to 1000 nm, and below 1 dB/cm in the region from 750 nm-1100 nm. The characterization was carried out by coupling light using a 50 μm fiber into a waveguide of 6 cm length and a cross section of 40 um×40 um and picking up the light, again using a an optical fiber at the opposite facet of the waveguide.

Figure 7:
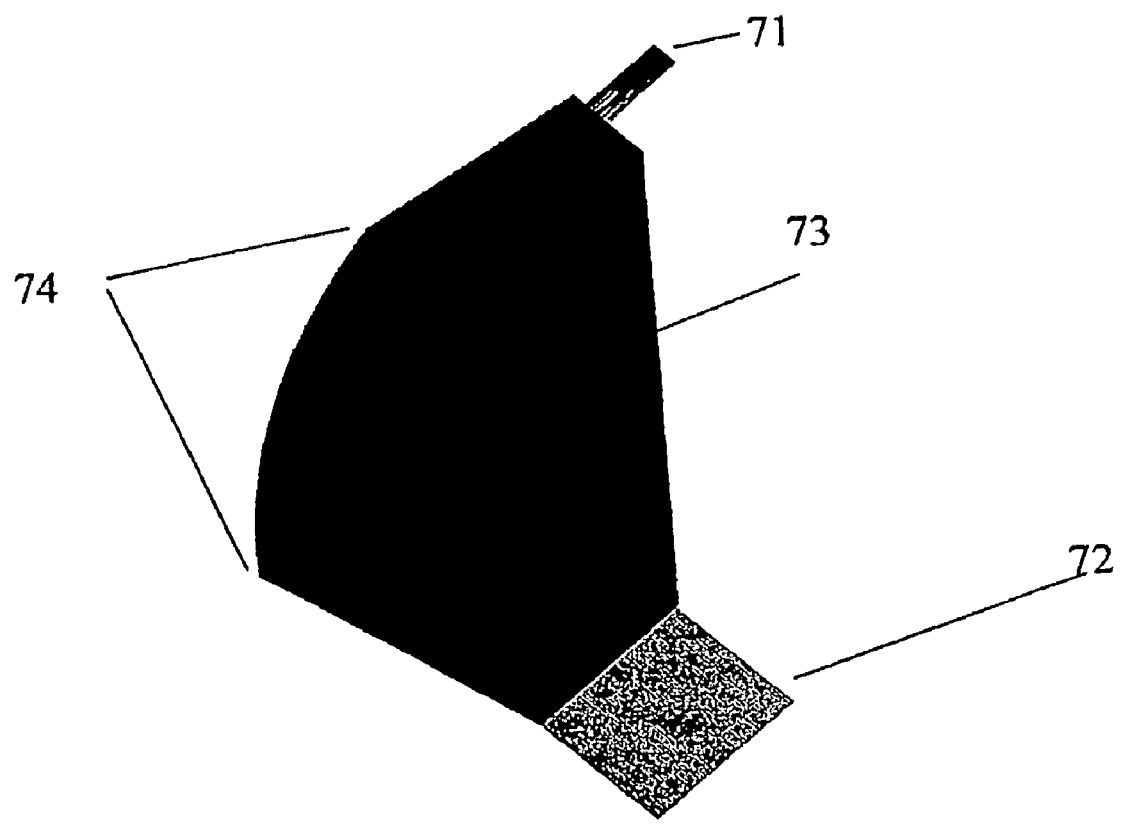
FIG. 7 shows a mask structure for manufacturing of a spectrometer.

FIG. 7 shows the shape 70 of a spectroscope including input waveguide 71, output waveguide 72, slab waveguide 73 and grating 74. The grating groove 75 is also illustrated, the height of the groove need not be constant over the full grating. This shape may also be used as the mask for the photoresist as described above, thus providing the entire spectroscope in one process. The microfluidic channel may be added to the mask, negative of the waveguides so that the channel is formed upon developing of the structure. The grating is not easily seen on the mask, but is formed of a number of grooves in the curved part of the slab waveguide.

Figure 8:
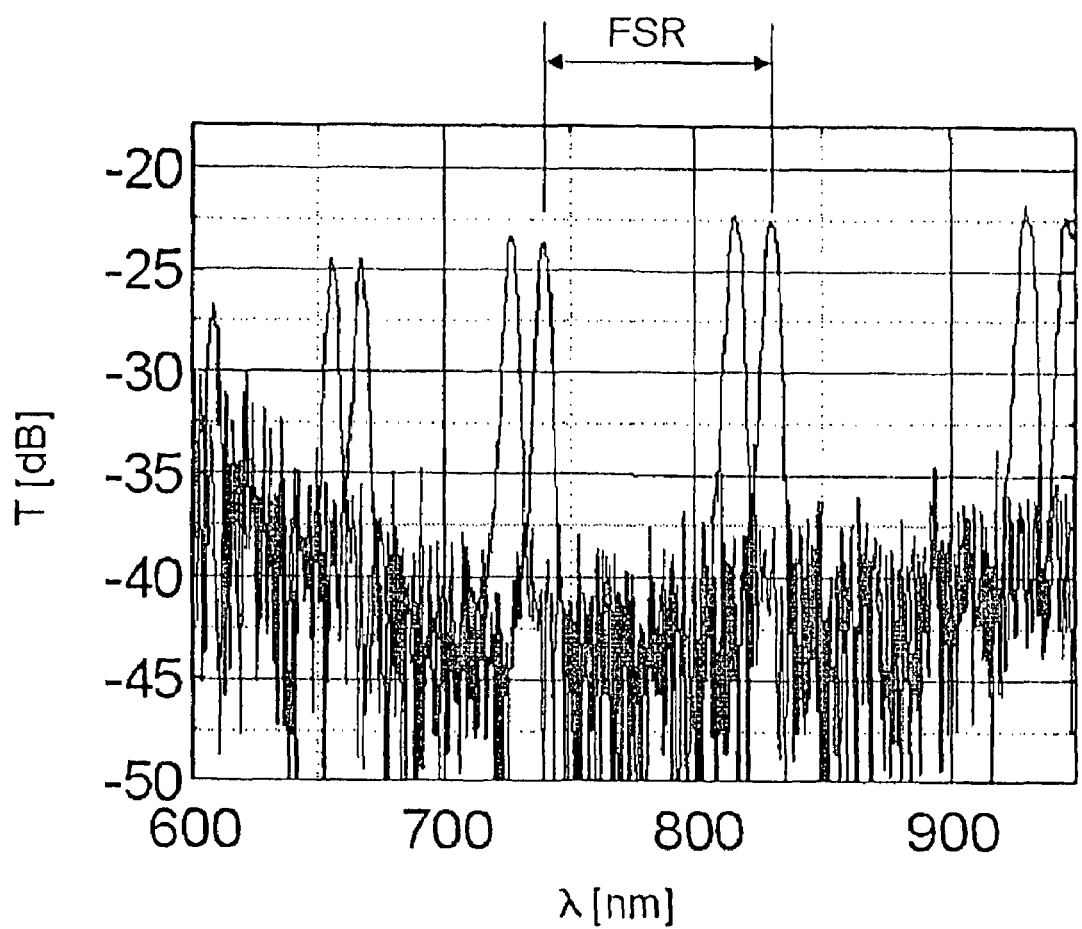
FIG. 8 shows a spectroscope output for a spectroscope working in the 9th order.
Figure 9:
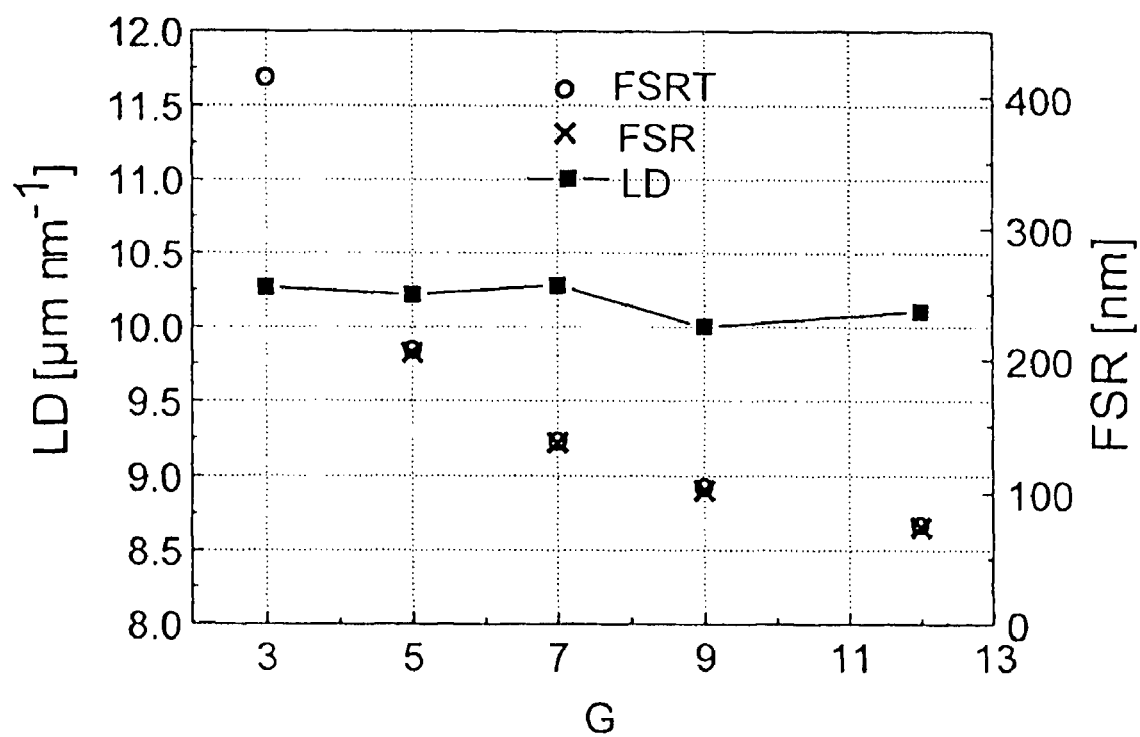
FIG. 9 shows the measured linear dispersion of the system.

In FIG. 8, a spectroscope output, or transmission T, is shown for a spectroscope working in the 7th order giving counts as a function of wavelength. The two curves correspond to two different pick-up positions at the spectroscope output facet. A broad band light source was used as spectrometer input. The outcoming light is spectrally distributed over the output facet and by placing a fiber at different positions along the output facet, it is possible to pick up the different wavelengths and a characteristic response function for the spectroscope is provided. There is in this characterized spectroscope no entrance or output slit for which reason the spectral response is rather broad. The two peaks of each curve correspond to two different orders of the grating and the distance between them thereby defining the free spectral range, FSR, of the grating, which in FIG. 8 is about 95 nm Another parameter, which is of importance for the spectroscope is the linear dispersion, LD. In FIG. 9, a measured linear dispersion (μm/nm) is shown as a function of the wavelength and versus the grating order, G, for a number of spectrometers with different grating order. The linear dispersion is a measurement of wavelength changes across the output of the spectrometer. The spectrometers are designed to operate with the same LD and as can be seen they have approximately the same value of about 10 μn/nm. This means that for two channels separated by 100 μm the light in the two will have a wavelength difference of 10 nm. The plot includes both the theoretical values (FSRT:Circles) and the actual measured ones (FSR:crosses).

Figure 10:
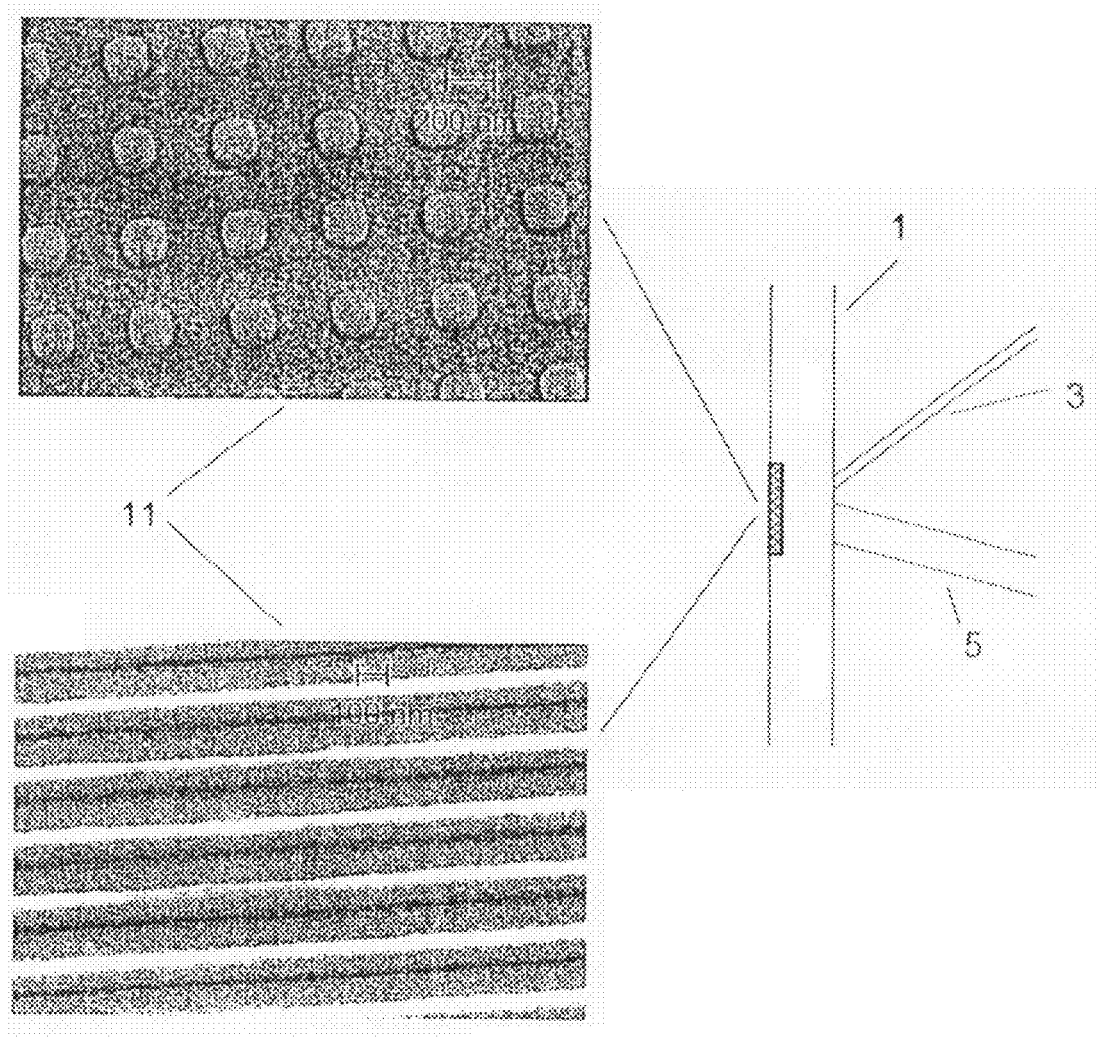
FIG. 10 shows a microfluidic channel with nanostructured channel walls for SERS measurements.

FIG. 10 illustrates a microfluidic channel having a nanostructured wall. The side wall of the channel comprise a SERS active region 11. The region may either be illuminated through a lid or the substrate of the structure, or through the waveguide 3. The amplified Raman signal is then collected by the waveguide 5. The nanostructured surface may be a random nanostructure, such as a rough surface, such as a rough silver surface, or it may be an ordered structure, where the nanoparticles form a surface grid with controllable dimensions. Two SEM pictures of ordered SERS active surface are shown as examples. The SEM pictures are of electron beam lithographic patterns in photoresist covered with gold. The dimensions of the structures are approximately 100 nm to 800 nm and the separation between them can be as little as 20 nm and up to 800 nm. Dots, holes and lines as well as other geometrical structures can be used. The pick-up of the SERS signal is done by a waveguide, an interconnecting waveguide, which guides the light signals into the spectroscope. The advantage of using SERS and not just ordinary Raman spectroscopy is due to the effective enhancement of the signals so that a Raman signal may be enhanced many orders of magnitude.

Although the present invention has been described in connection with preferred embodiments, it is not intended to be limited to the specific form set forth herein. Rather, the scope of the present invention is limited only by the accompanying claims.

In this section, certain specific details of the disclosed embodiment are set forth for purposes of explanation rather than limitation, so as to provide a clear and thorough understanding of the present invention. However, it should be understood readily by those skilled in this art, that the present invention may be practiced in other embodiments which do not conform exactly to the details set forth herein, without departing significantly from the spirit and scope of this disclosure. Further, in this context, and for the purposes of brevity and clarity, detailed descriptions of well-known apparatus, circuits and methodology have been omitted so as to avoid unnecessary detail and possible confusion.

The invention claimed is:

1. A micro total analysis system comprising a spectroscope provided on a substrate and for measuring electromagnetic radiation, the spectroscope comprising:
   (a) a slab waveguide for guiding electromagnetic waves towards a diffraction grating dispersing the electromagnetic waves into their component wavelengths,
   (b) output means for receiving the deflected electromagnetic waves, and
   (c) at least one microfluidic channel,
   wherein the at least one microfluidic channel, the slab waveguide and the grating are each comprised of the same main material and are molded to form one piece.

2. A system according to claim 1, wherein the main material is selected from the group consisting of polycarbonate PC and cyclo-olefin-copolymer COC.

3. A system according to claim 1, wherein the at least one microfluidic channel, the slab waveguide and the grating are manufactured in a material suitable for molding.

4. A system according to claim 1, wherein the spectroscope and the at least one microfluidic channel are interconnected by an interconnecting waveguide guiding electromagnetic waves from the at least one microfluidic channel to the slab waveguide.

5. A system according to claim 4, wherein the interconnecting waveguide comprises the same main material or is manufactured forming a monolithic element with the at least one microfluidic channel, the slab waveguide and the grating.

6. A system according to claim 1, wherein the at least one microfluidic channel comprises an analyzation part, and wherein electromagnetic radiation is emitted from or transmitted through the analyzation part of the channel.

7. A system according to claim 4, wherein the interconnecting waveguide is adapted to receive the electromagnetic radiation emitted from or transmitted through the at least one microfluidic channel.

8. A system according to claim 7, wherein the electromagnetic radiation is emitted from or transmitted through the at least one microfluidic channel in response to an incoming electromagnetic wave.

9. A system according to claim 1, wherein the electromagnetic waves propagate within the main material and the effect of total internal reflection is utilized to deflect the light towards the output means.

10. A system according to claim 4, wherein a tapered section of the interconnecting waveguide positioned adjacent to the slab waveguide form an entrance slit to the slab waveguide.

11. A system according to claim 4, wherein the interconnecting waveguide comprises a light frequency dependent element.

12. A system according to claim 4, wherein the grating is positioned in the slab waveguide opposite the interconnecting waveguide.

13. A system according to claim 1, wherein the output means are positioned substantially opposite to (180°), substantially rectangular (90°) or at an angle in the interval between 0 to 20° to the grating.

14. A system according to claim 1, wherein a shape and angle of grating grooves are adjusted in such a way that total reflection of the incoming electromagnetic waves grating is maximized.

15. A system according to claim 1, wherein the grating is provided in the slab waveguide simultaneous with the manufacturing of the slab waveguide.

16. A system according to claim 1, wherein grooves defining the grating are 10 µm-50 µm deep, transverse to a surface of the slab waveguide.

17. A system according to claim 1, wherein the output means comprises waveguides or an array of waveguides.

18. A system according to claim 1, wherein the output means connects to one or more light sensitive semiconductor devices.

19. A system according to claim 1, wherein the substrate is a silicon substrate.

20. A system according to claim 19, wherein the output means connects to one or more light sensitive semiconductor devices being formed integrated with the silicon substrate.

21. A system according to claim 4, wherein the interconnecting waveguide is a multimode waveguide.

22. A system according to claim 1, wherein electromagnetic radiation is emitted from or transmitted through the at least one microfluidic channel in response to an incoming electromagnetic wave, and wherein the incoming electromagnetic wave is emitted from an external light source.

23. A system according to claim 1, wherein electromagnetic radiation is emitted from or transmitted through the at least one microfluidic channel in response to an incoming electromagnetic wave, and wherein the incoming electromagnetic wave is emitted from a light source integrated with the micro total analysis system or provided on the same substrate.

24. A system according to claim 1, wherein the at least one microfluidic channel comprises at least one area with a nanostructured surface.

25. A system according to claim 24, wherein the nanostructured surface is metallized.

26. A system according to claim 25, wherein the metal comprises Au, Ag, Cu or any combination thereof.

27. A system according to claim 24, wherein the nanostructured surface provides an amplification of a Raman signal.

28. A system according to claim 24, wherein the spectroscope and the at least one microfluidic channel are interconnected by an interconnecting waveguide guiding electromagnetic waves from the at least one microfluidic channel to the slab waveguide, and wherein scattered light from the nanostructured surface is collected from the nanostructured surface and guided through the interconnecting waveguide to the spectroscope.

29. A system according to claim 23, wherein the spectroscope and the at least one microfluidic channel are interconnected by an interconnecting waveguide guiding electromagnetic waves from the at least one microfluidic channel to the slab waveguide, and wherein the incoming electromagnetic wave is directed towards an area of the at least one microfluidic channel in electromagnetic communication with the interconnecting waveguide.

30. A system according to claim 4, wherein the height of the interconnecting waveguide and the depth of the at least one microfluidic channel are substantially the same.

31. A system according to claim 30, wherein the numerical aperture of the waveguide is selected so as to maximize electromagnetic radiation coupled from the at least one microfluidic channel to the interconnecting waveguide.

32. A system according to claim 1, wherein the molding technique is an injection molding technique.

33. A system according to claim 1, wherein the molding technique is an embossing molding technique.

* * * * *